US012434051B2

(12) United States Patent
Hill et al.

(10) Patent No.: US 12,434,051 B2
(45) Date of Patent: Oct. 7, 2025

(54) COMPRESSION GARMENT ASSEMBLY FOR APPLYING TTFIELDS AND METHODS OF PRODUCTION AND USE THEREOF

(71) Applicant: Novocure GmbH, Root (CH)

(72) Inventors: Christopher Hill, San Francisco, CA (US); Woonghee Han, San Francisco, CA (US); Darja Wendel, San Francisco, CA (US)

(73) Assignee: Novocure GmbH, Root (CH)

(*) Notice: Subject to any disclaimer, the term of this patent is extended or adjusted under 35 U.S.C. 154(b) by 402 days.

(21) Appl. No.: 18/062,421

(22) Filed: Dec. 6, 2022

(65) Prior Publication Data

US 2023/0181898 A1 Jun. 15, 2023

Related U.S. Application Data

(60) Provisional application No. 63/288,201, filed on Dec. 10, 2021.

(51) Int. Cl.
*A61N 1/04* (2006.01)
*A61B 18/00* (2006.01)
(Continued)

(52) U.S. Cl.
CPC ....... *A61N 1/36002* (2017.08); *A61N 1/0484* (2013.01); *A61N 1/40* (2013.01); *A61B 2018/0016* (2013.01)

(58) Field of Classification Search
CPC .... A61N 1/0484; A61N 1/046; A61N 1/0496; A61N 1/3987; A61N 1/0456;
(Continued)

(56) References Cited

U.S. PATENT DOCUMENTS

| | | | |
|---|---|---|---|
| 6,148,233 | A | 11/2000 | Owen et al. |
| 6,711,427 | B1 | 3/2004 | Ketelhohn |

(Continued)

FOREIGN PATENT DOCUMENTS

| | | | |
|---|---|---|---|
| CN | 111013008 | A | 4/2020 |
| CN | 111481823 | A | 8/2020 |

OTHER PUBLICATIONS

Kirson, et al. "Disruption of Cancer Cell Replication by Alternating Electric Fields," *Cancer Research*, May 1, 2004, vol. 64, pp. 3288-3295.

(Continued)

*Primary Examiner* — Carl H Layno
*Assistant Examiner* — Anh-Khoa N Dinh
(74) *Attorney, Agent, or Firm* — DUNLAP CODDING, P.C.

(57) ABSTRACT

A garment is herein disclosed. In some implementations, the garment may comprise a support layer configured to be worn by a patient. The support layer may be sized and dimensioned to cover at least a portion of the patient and associated with a transducer array fastener. A transducer array may have a skin-facing surface and a complementary array fastener associated with a surface opposite the skin-facing surface. The transducer array fastener may be operable to be coupled with the complementary array fastener. The transducer array may have a first edge, a second edge opposite the first edge; and a protective layer disposed on the skin-facing surface of the transducer array. The protective layer may have a release member extending from the protective layer adjacent to the first edge of the transducer array and extends beyond the second edge of the transducer array.

19 Claims, 9 Drawing Sheets

(51) Int. Cl.
*A61N 1/36* (2006.01)
*A61N 1/40* (2006.01)

(58) Field of Classification Search
CPC .. A61N 1/36031; A61N 1/36117; A61N 7/00; A61B 5/256; A61B 5/266; A61B 5/27; A61B 5/28; A61B 5/6804; A61B 2562/029; A61B 5/0022; A61B 5/02055; A61B 5/02108; A61B 5/02241; A61B 5/02416; A61B 5/0531; A61B 5/0533; A61B 5/11
See application file for complete search history.

(56) References Cited

U.S. PATENT DOCUMENTS

| | | | | |
|---|---|---|---|---|
| 7,016,725 | B2 | 3/2006 | Palti | |
| 7,089,054 | B2 | 8/2006 | Palti | |
| 7,333,852 | B2 | 2/2008 | Palti | |
| 7,565,205 | B2 | 7/2009 | Palti | |
| 7,805,201 | B2 | 9/2010 | Palti | |
| 8,244,345 | B2 | 8/2012 | Palti | |
| 2006/0237019 | A1 | 10/2006 | Palti | |
| 2018/0001101 | A1* | 1/2018 | Hulings | A61N 1/046 |
| 2020/0061366 | A1* | 2/2020 | Decker | A61N 1/0492 |
| 2021/0346693 | A1 | 11/2021 | Deslauriers | |
| 2022/0096819 | A1 | 3/2022 | Wasserman et al. | |
| 2022/0193404 | A1 | 6/2022 | Wasserman | |

OTHER PUBLICATIONS

EPO acting as International Searching Authority; International Search Report and Written Opinion in PCT/IB2022/061942, dated Feb. 14, 2023, filed Dec. 8, 2022.

* cited by examiner

COMPRESSION GARMENT ASSEMBLY FOR APPLYING TTFIELDS AND METHODS OF PRODUCTION AND USE THEREOF

CROSS-REFERENCE TO RELATED APPLICATIONS

This application is a non-provisional application claiming benefit to the U.S. Provisional Application No. 63/288,201 filed on Dec. 10, 2021. The entire content of the above-referenced application is hereby incorporated herein by reference in its entirety.

BACKGROUND

Tumor Treating Fields (TTFields) therapy is a proven approach for treating tumors. For example, using the Optune® system for delivering tumor treating fields, the TTFields are delivered to patients via four transducer arrays placed on the patient's skin in close proximity to a tumor. The transducer arrays are arranged in two pairs, and each transducer array is connected via a multi-wire cable to an electric field generator. The electric field generator (a) sends an AC current through one pair of arrays during a first period of time; then (b) sends an AC current through the other pair of arrays during a second period of time; then repeats steps (a) and (b) for the duration of the treatment.

SUMMARY OF THE DISCLOSURE

It is desirable for a system and method to assist a patient in placing and maintaining the transducer arrays at predetermined locations on the patient's body. It is to such a system and method the present disclosure is directed.

In some embodiments, the problem of assisting the patient in placing the transducer arrays and maintaining a sufficient electrical connection between the transducer arrays and the patient's body at predetermined locations on the patient is solved by a garment, comprising: a support layer configured to be worn by a patient, the support layer sized and dimensioned to cover at least a portion of the patient and associated with a transducer array fastener; a transducer array having a skin-facing surface and a complementary array fastener associated with a surface opposite the skin-facing surface, the transducer array fastener operable to be coupled with the complementary array fastener; and a protective layer disposed on the skin-facing surface of the transducer array, the protective layer having a release member extending from the protective layer at a first edge of the transducer array and extending beyond a second edge of the transducer array, the second edge being opposite the first edge.

The details of one or more implementations of the subject matter described in this specification are set forth in the accompanying drawings and the description below. Other aspects, features and advantages of the subject matter will become apparent from the description, the drawings, and the claims.

BRIEF DESCRIPTION OF THE DRAWINGS

The accompanying drawings, which are incorporated in and constitute a part of this specification, illustrate one or more implementations described herein and, together with the description, explain these implementations. The drawings are not intended to be drawn to scale, and certain features and certain views of the figures may be shown exaggerated, to scale or in schematic in the interest of clarity and conciseness. Not every component may be labeled in every drawing. Like reference numerals in the figures may represent and refer to the same or similar element or function. In the drawings.

DETAILED DESCRIPTION

Figure 1A:
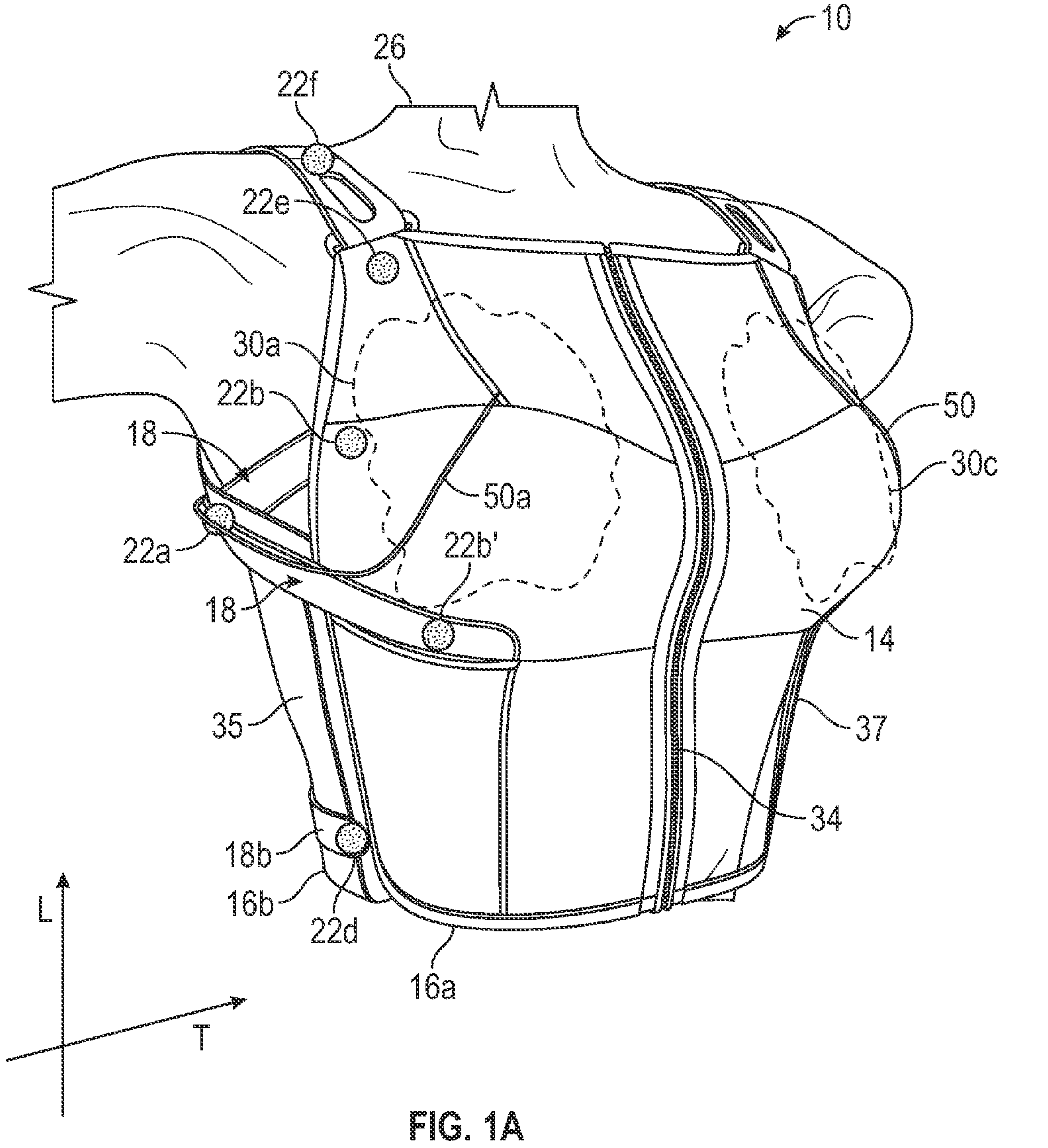
FIG. 1A is a front perspective view of an exemplary embodiment of a garment constructed in accordance with the present disclosure.

TTFields are generally delivered to patients via four transducer arrays placed on the patient's skin conventionally as two orthogonal pairs in locations chosen to best target the tumor (target region). Each transducer array is configured as a set of coupled electrode elements (for example, about 2 cm in diameter) that are interconnected via flex wires. When placing the arrays on the patient, medical gel adheres to the contours of the patient's skin and ensures good electrical contact of the device with the body.

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed inventive concept(s) shall have the meanings that are commonly understood by those of ordinary skill in the art. Further, unless otherwise required by context, singular terms shall include pluralities and plural terms shall include the singular.

All of the compositions, assemblies, systems, kits, and/or methods disclosed herein can be made and executed without undue experimentation in light of the present disclosure. While the compositions, assemblies, systems, kits, and methods of the inventive concept(s) have been described in terms of particular embodiments, it will be apparent to those of skill in the art that variations may be applied to the compositions and/or methods and in the steps or in the sequence of steps of the methods described herein without departing from the concept, spirit, and scope of the inventive concept(s). All such similar substitutions and modifications apparent to those skilled in the art are deemed to be within the spirit, scope, and concept of the inventive concept(s) as defined by the appended claims.

Unless otherwise expressly stated, it is in no way intended that any method or aspect set forth herein be construed as requiring that its steps be performed in a specific order. Accordingly, where a method claim does not specifically state in the claims or description that the steps are to be limited to a specific order, it is no way intended that an order be inferred, in any respect.

Headings are provided for convenience only and are not to be construed to limit the invention in any manner. Embodiments illustrated under any heading or in any portion of the disclosure may be combined with embodiments illustrated under the same or any other heading or other portion of the disclosure. Any combination of the elements described herein in all possible variations thereof is encompassed by the disclosure unless otherwise indicated herein or otherwise clearly contradicted by context.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, or greater numbers of compounds. The term "plurality" refers to "two or more."

The use of the term "at least one" will be understood to include one as well as any quantity more than one. The use of ordinal number terminology (i.e., "first," "second," "third," "fourth," etc.) is solely for the purpose of differentiating between two or more items and does not imply any sequence or order or importance to one item over another or any order of addition.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" in various places in the specification is not necessarily all referring to the same embodiment, for example.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "patient" as used herein encompasses any mammals including human and veterinary subjects. "Mammal" for purposes of treatment refers to any animal classified as a mammal, including (but not limited to) humans, domestic and farm animals, nonhuman primates, and any other animal that has mammary tissue. In some embodiments, the term "patient" may apply to a simulation mannequin for use in teaching, for example.

Circuitry, as used herein, may be analog and/or digital components, or one or more suitably programmed processors (e.g., microprocessors) and associated hardware and software, or hardwired logic. Also, "components" may perform one or more functions. The term "component," may include hardware, such as a processor (e.g., microprocessor), an application specific integrated circuit (ASIC), a field programmable gate array (FPGA), a combination of hardware and software, and/or the like. The term "processor" as used herein means a single processor or multiple processors working independently or together to perform a task.

The term "TTField", as used herein, means tumor treating field. TTFields are low intensity (e.g., 1-4 V/cm) alternating electric fields of medium frequencies (about 50 kHz to about 1 MHz, and more preferably from about 50 kHz to about 500 kHz) that when applied to a conductive medium, such as a human body, via electrodes, may be used, for example, to treat tumors, as described in U.S. Pat. Nos. 7,016,725; 7,089,054; 7,333,852; 7,565,205; 7,805,201; and 8,244,345 by Palti; and in "Disruption of Cancer Cell Replication by Alternating Electric Fields", by Eilon D. Kirson et al., *Cancer Res.* 2004 64:3288-3295, all of which are hereby expressly incorporated by reference herein in their entirety. TTFields have been shown to have the capability to specifically affect cancer cells and serve, among other uses, for treating cancer. TTFields therapy is an approved monotreatment for recurrent glioblastoma (GBM), and an approved combination therapy with chemotherapy for newly diagnosed GBM patients.

The term "transducer array", as used herein, means a conductive transducer array or a non-conductive transducer array. Exemplary transducer arrays may include, for example, pads disclosed in any one of U.S. Patent Publication No. 2021/0346693 entitled "CONDUCTIVE PAD GENERATING TUMOR TREATING FIELD AND METHODS OF PRODUCTION AND USE THEREOF" and U.S. patent application Ser. No. 63/128,265 entitled "OPTIMIZATION OF COMPOSITE ELECTRODE", all of which are hereby expressly incorporated by reference herein in their entirety.

Referring now to the drawings, and in particular FIG. 1A, shown therein is a front perspective view of an exemplary embodiment of a garment 10 constructed in accordance with the present disclosure. The garment 10 generally comprises a support layer 14, a first adjustment assembly 18, and two or more connection points 22*a-n*, referred to generally as connection points 22 and individually as connection point 22, are illustrated in FIG. 1A as first connection point 22*a* and second connection point 22*b*. Though the connection points 22*a-n* are referred to herein as points for explanatory purposes, it will be understood that the connection points 22*a-n* may have a length, a width, and an area. In some embodiments, one or more of the connection points 22*a-n* may have one or more openings.

As shown in FIG. 1A, the garment 10 is shown in use by a patient 26 whereby the support layer 14 supports one or more transducer array 30*a-n*, referred to generally as transducer arrays 30 and individually as transducer array 30, over a treatment area of the patient 26. In this example, the garment 10 supports first, second, third, and fourth transducer arrays 30*a*, 30*b*, 30*c*, 30*d*, though it will be understood that more or fewer transducer arrays 30*a-n* may be used.

In one embodiment, the garment 10 covers the torso of the patient 26, as shown in FIG. 1A. In this embodiment, the garment 10 may be one or more of an undergarment, a shirt, tank-top, jacket, vest, sweater, and/or the like. In other embodiments, the garment 10 covers a different part of the patient 26, such as, one or more of the patient's head, arm, waist, leg, hand, or foot. For example, the garment 10 may be a head covering (such as a hat), an arm covering (such as a sleeve), a hand covering (such as a glove), a foot covering (such as a sock or shoe), a leg or waist covering (such as pants, shorts, stockings), or the like.

Throughout this application, the garment 10 may be described as being a vest, vest-like, or having features of a vest, however, the garment 10 is not limited to being a vest, as described above.

In one embodiment, the garment 10 is "breathable", that is, the garment 10 includes one or more perforation configured to allow air to move through the garment 10 to the patient 26, such as to contact the patient's skin, for example. In other embodiments, the garment 10 may be "wicking", that is, the garment 10 may be constructed to allow sweat or moisture near the patient's skin to be removed, or wicked, from the patient 26 through the garment 10.

In one embodiment, as shown in FIG. 1A, the garment 10 may be configured to be worn under outer clothing by the patient 26. For example, the garment 10 may be an undergarment and the patient 26 may wear a shirt over the garment 10. In this embodiment, the garment 10 may be considered form-fitting, such that when the patient 26 wears a shirt over the garment 10, a third-party viewing the patient is unlikely to notice that the patient 26 is wearing the garment 10, thereby providing the patient 26 privacy of treatment while using the garment 10. Such privacy may have benefits for the patient 26, such as providing the patient 26 with confidence to continue with normal, daily activities during treatment without concern of third-parties noticing the treatment.

The support layer 14 is configured to be worn by the patient 26 and may comprise a front portion 16*a* and a back portion 16*b*. The support layer 14 is sized and dimensioned to cover at least a portion of the patient 26, preferably in a form-fitting manner. Further, the support layer 14 is configured to support the two or more connection points 22*a-n*. In one embodiment, the support layer 14 is constructed of a breathable material as described above, and may be, for example, constructed of a woven material (e.g., a woven fabric), a mesh material, or the like. In other embodiments, the support layer 14 may be constructed of a non-woven material (e.g., a non-woven fabric).

In one embodiment, the support layer 14 may be considered form-fitting, that is, the support layer 14 may be configured to conform to the patient 26 when the patient is wearing the garment 10.

In one embodiment, the support layer 14 covers the torso of the patient 26, as shown in FIG. 1A. In this embodiment, the support layer 14 may be one or more of an undergarment, a shirt, tank-top, jacket, vest, sweater, and/or the like. In other embodiments, the support layer 14 covers a different part of the patient 26, such as, one or more of the patient's head, arm, waist, leg, hand, or foot. For example, the support layer 14 may be a head covering (such as a hat), an arm covering (such as a sleeve), a hand covering (such as a glove), a foot covering (such as a sock or shoe), a leg or waist covering (such as pants, shorts, stockings), or the like.

Throughout this application, the support layer 14 may be described as being a vest, vest-like, or having features of a vest, however, the support layer 14 is not limited to being a vest, as described above.

In one embodiment, the support layer 14 is "breathable", that is, the support layer 14 includes one or more perforation configured to allow air to move through the support layer 14 to the patient 26, such as to contact the patient's skin, for example. In other embodiments, the support layer 14 may be "wicking", that is, the support layer 14 may be constructed to allow sweat or moisture near the patient's skin to be removed, or wicked, from the patient 26 through the support layer 14.

In one embodiment, as shown in FIG. 1A, the support layer 14 may be configured to be worn under outer clothing by the patient 26. For example, the support layer 14 may be an undergarment and the patient 26 may wear a shirt over the support layer 14. In this embodiment, the support layer 14 may be considered form-fitting, such that when the patient 26 wears a shirt over the support layer 14, a third-party viewing the patient is unlikely to notice that the patient 26 is wearing the support layer 14, thereby providing the patient 26 privacy of treatment while using the garment 10. Such privacy may have benefits for the patient 26, such as providing the patient 26 with confidence to continue with normal, daily activities during treatment without concern of third-parties noticing the treatment.

In some embodiments, a first portion of the support layer 14 and a second portion of the support layer 14 are constructed of either different materials or of the same material exhibiting differing properties.

In one embodiment, the first adjustment assembly 18 is adjustably secured to the support layer 14 at the first connection point 22*a* on the back portion 16*b* and the second connection point 22*b* on the front portion 16*a* such that adjustment of the first adjustment assembly 18 varies a spacing between the first connection point 22*a* and the second connection point 22*b* thereby varying a tension of the support layer 14 in at least a portion of the treatment area. In one embodiment, the first adjustment assembly 18 is adjustable between a first position exerting a first force 70*a* (shown in FIG. 2A) in a direction extending from the second connection point 22*b* to the first connection point 22*a*, and a second position. However, it will be understood that in some embodiments, the first force 70*a* may be in a direction extending from the first connection point 22*a* to the second connection point 22*b*.

In one embodiment, the first adjustment assembly 18 may be, in addition to or instead of being adjustably secured to the first connection point 22*a*, further adjustably secured at a third connection point 22*b*' on the front portion 16*a* such that adjustment of the first adjustment assembly 18 varies the spacing between the third connection point 22*b*' and one or more of the second connection point 22*b* and the first connection point 22*a*, thereby further varying the tension of the support layer 14 in at least the portion of the treatment area. In one embodiment, the first adjustment assembly 18 is adjustable between the first position and the second position thereby exerting the first force 70*a* (shown in FIG. 2A) in the direction extending from the second connection point 22*b* to the first connection point 22*a* and exerting a second force 70*a*' in a direction extending from the third connection point 22*b*' to the second connection point 22*b*. However, it will be understood that in some embodiments, the second force 70*a*' may be in a direction extending from the second connection point 22*b* to the third connection point 22*b*'. In some embodiments, the first adjustment assembly 18 may be adjustably secured from the second connection point 22*b* through the first connection point 22*a* to the third connection point 22*b*'. In some embodiments, one or more of the connection points 22*a-n*, such as the first connection point 22*a*, may be configured such that the first adjustment assembly 18 moves through a portion of the connection point 22*a-n*. For example, one or more of the connection points 22*a-n* may have a loop, slot, or other opening, configured to slidably receive the first adjustment assembly 18.

By applying force to the support layer 14, the support layer 14 presses against the transducer array(s) 30 thereby assisting in maintaining the sufficient electrical connection between the transducer array(s) 30 and the patient's body. The sufficient electrical connection between the transducer array(s) 30 and the patient's body can be measured as the impedance between two or more of the transducer arrays 30*n*. In some embodiments, the impedance should be between 20 Ohms and 160 Ohms.

The first, second, and third connection points 22*a*, 22*b*, 22*b*' may be associated with the support layer 14 and the first adjustment assembly 18. In one embodiment, the first connection point 22*a* may be at a fixed location in or on the back portion 16*b* of the support layer 14 at a first vertical position along a longitudinal axis L and a first horizontal position along a transverse axis T, whereas the second connection point 22*b* may be at an adjustable location in or on the front portion 16*a* of the support layer 14 at a second vertical position along the longitudinal axis L and a second horizontal position along the transverse axis T where the second vertical position is vertically displaced along the longitudinal axis L from the first vertical position and the second horizontal position is horizontally displaced along the transverse axis T from the first horizontal position.

In one embodiment, as shown in FIG. 1A, the first adjustment assembly 18 may be a strap extending between the front portion 16*a* and the back portion 16*b* of the support layer 14, e.g., between the first connection point 22*a* and the second connection point 22*b*, and/or from the second connection point 22*b* through the first connection point 22*a* to the third connection point 22*b*'. In one embodiment, the first connection point 22*a* may be at a fixed location on the back portion 16*b* of the support layer 14. In one embodiment, the second connection point 22*b* may be at a fixed location on the front portion 16*a* of the support layer. For example, an end of the strap may be sewn, or otherwise attached, to the support layer 14. In other embodiments, the second connection point 22*b* and/or the third connection point 22*b*' may be a first component of a hook and loop fastener while a second component of the hook and loop fastener is integrated with the strap. The strap, therefore, may be adjustably attached to the first component of the hook and loop fastener. The first adjustment assembly 18, shown in FIG. 1A is in a first position.

As described above, a patient is any mammal including a human or a veterinary subject. The patient 26 may be any mammal; however, the patient 26 will be referred to as a human and having human properties. It is understood, however, that the patient 26 may be any mammal and that the garment 10 may be configured to be worn by, or placed on, a patient 26 that is other than a human.

The one or more transducer array 30*a-n*, shown in FIG. 1A as the first transducer array 30*a*, is a field-generating transducer array, such as one of the transducer arrays incorporated above. The transducer arrays 30 may be configured to generate a TTField when connected to an electric field generator such as the electric field generator described in one or more of U.S. Pat. Nos. 7,016,725, 7,089,054, 7,333, 852, 7,565,205, 7,805,201, and 8,244,345 by Palti.

In one embodiment, the garment 10 may further include a fastening component 34. The fastening component 34 may be configured to allow the patient 26 to remove and/or re-attach the garment 10 without adjustment of the first adjustment assembly 18. In one embodiment, in order to adjustably secure the first adjustment assembly 18 to the support layer 14, the fastening component 34 is first engaged thereby ensuring that adjustment of the first adjustment assembly 18 is made from a known configuration thus enabling the patient 26 to take off/remove the garment 10 and put on/apply the garment 10 while maintaining tension of the support layer 14 over at least a portion of the treatment area.

In one embodiment, as shown in FIG. 1A, the fastening component 34 is a zipper bisecting the support layer 14 in a direction parallel with the longitudinal axis L and configured to pass over the patient's sternum when the garment 10 is worn by the patient. However, in other embodiments, the fastening component 34 may be otherwise constructed, such as with a plurality of buttons and button-holes, one or more hook and loop fastener, and/or the like.

Figure 1B:
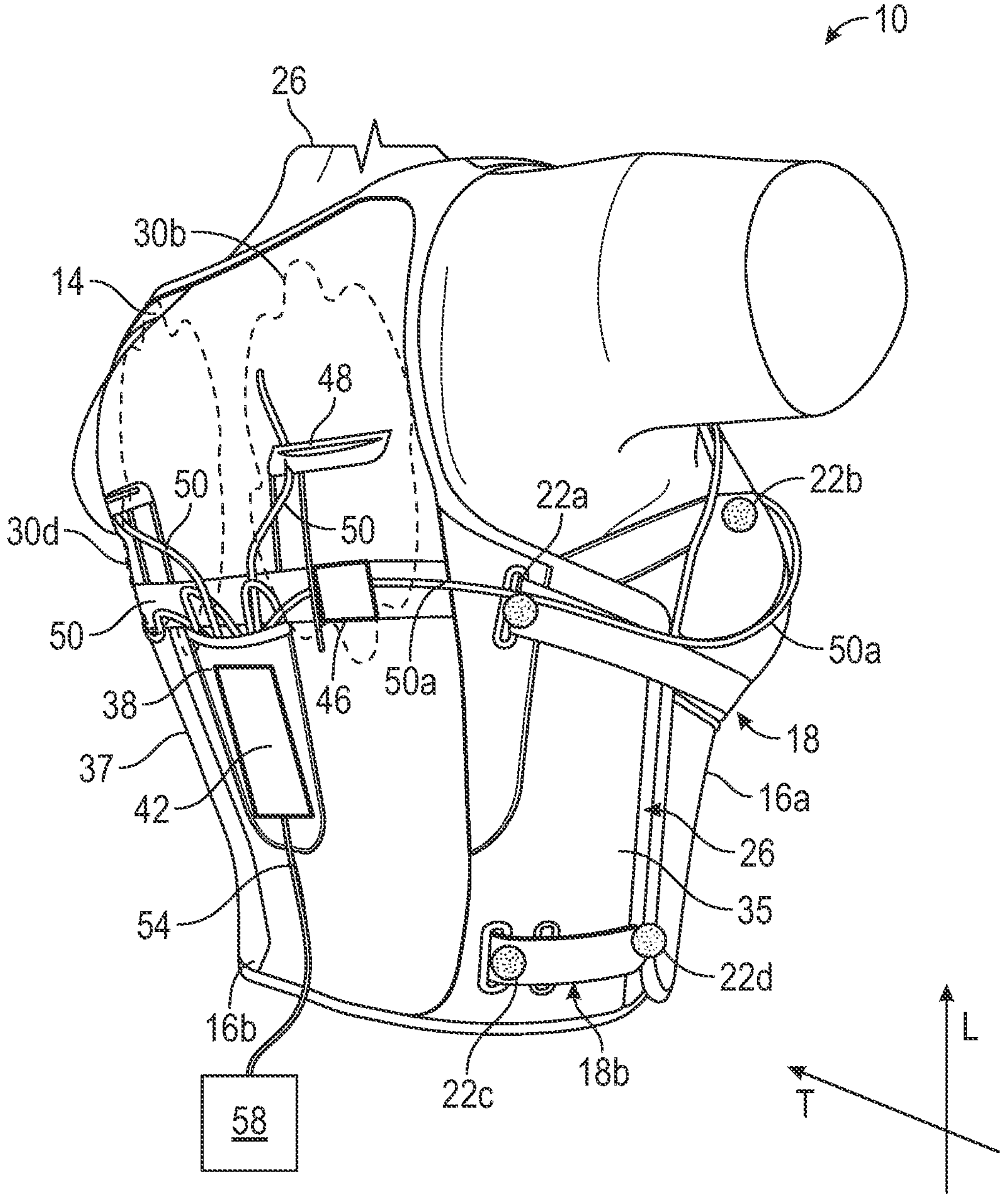
FIG. 1B is a rear perspective view of an exemplary embodiment of the garment of FIG. 1A constructed in accordance with the present disclosure.

Referring now to FIG. 1B, shown therein is a rear perspective view of an exemplary embodiment of the garment 10 constructed in accordance with the present disclosure. Shown in FIG. 1B, the garment 10 includes the first adjustment assembly 18 associated with the support layer 14 and the first connection point 22*a* on the back portion 16*b* of the support layer 14.

In one embodiment, the garment 10 is provided with a second adjustment assembly 18*b* adjustably secured to the support layer 14 at a fourth connection point 22*c* and a fifth connection point 22*d* such that adjustment of the second adjustment assembly 18*b* varies a spacing between the fourth connection point 22*c* and the fifth connection point 22*d* thereby varying a tension of the support layer 14. In one embodiment, the second adjustment assembly 18*b* is adjustable between a first position exerting a third force 70*b* (shown in FIG. 2A) in a direction extending from the fifth connection point 22*d* to the fourth connection point 22*c*, and a second position. However, it will be understood that in some embodiments, the third force 70*b* may be in a direction extending from the fourth connection point 22*c* to the fifth connection point 22*d*. In one embodiment, the second adjustment assembly 18*b* is a waist strap.

The fourth connection point 22*c* and the fifth connection point 22*d* may be different connection points 22 than the first connection point 22*a* and the second connection point 22*b*. In one embodiment, the fourth connection point 22*c* and the fifth connection point 22*d* are vertically displaced in the longitudinal axis L from the first vertical position of the first connection point 22*a* and the second vertical position of the second connection point 22*b*, respectively. The fifth connection point 22*d* may further be attached to the front portion 16*a* of the support layer 14 at a fourth horizontal position horizontally displaced along the transverse axis T from a third horizontal position of the fourth connection point 22*c* and the first horizontal position of the first connection point 22*a*. In one embodiment, the fourth connection point 22*c* and the fifth connection point 22*d* are vertically displaced below (towards the direction of the waist) from the first connection point 22*a* and the second connection point 22*b* on the back portion 16*b* and the front portion 16*a*, respectively.

In one embodiment, the garment 10 has a right side 35 and a left side 37, the left side 37 opposite the right side 35 across an approximately medial line parallel to the longitudinal axis L, and one or more of the first, second, third, fourth, and/or fifth connection point 22*a*, 22*b*, 22*b*', 22*c*, 22*d*, and/or the first adjustment assembly 18 and the second adjustment assembly 18*b* are duplicated on both the right side 35 and the left side 37 of the garment.

In one embodiment, the garment 10 further includes the second transducer array 30*b* adjustably affixed to the support layer 14 as described in more detail below in reference to FIG. 3A.

In one embodiment, as shown in FIG. 1B, the garment 10 further includes a hub support 38 configured to carry a hub 42. The hub support 38 may be formed as a pocket integrated with the support layer 14 positioned in the back portion 16*b* of the support layer 14 configured to cover a middle of the patient's back, for example. The hub support 38 may be a pocket operable to receive the hub 42. The hub support 38 may be formed of the same or different material as the support layer 14 and, in some embodiment, may be formed of breathable material to provide ventilation for the hub 42. Further, in one embodiment, the hub support 38 may extend over a portion of the support layer 14 that further includes a hub support backing attached thereto.

In one embodiment, as shown in FIG. 1B, the garment 10 further includes a lead guide 46 positioned on the back portion 16*b* of the support layer 14 configured to cover a mid-region on the patient's back. The lead guide 46 may be a loop of material configured to receive and guide one or more lead 50*a-n*, referred to generally as leads 50 and individually as lead 50, from transducer arrays 30 to the hub 42. The leads 50*a-n* may extend from corresponding ones of the transducer arrays 30*a-n* through the lead guide 46 and connect to the hub. For example, a first lead 50*a* may extend from the first transducer array 30*a*, through the lead guide 46 and connect to the hub 42. In one embodiment, the support layer 14 includes one or more aperture 48 through which the leads 50 may pass through the support layer 14.

Further shown in FIG. 1B is a cable 54 extending from, and electrically connecting, the hub 42 to an electric field generator 58. In one embodiment, the hub 42 is electrically coupled to each transducer array 30 via a separate one of the lead 50 and electrically coupled to the electric field generator 58, thereby communicably coupling the electric field generator 58 to one of more of the transducer arrays 30 enabling the electric field generator 58 to transmit one or more signal to the transducer arrays 30 causing the transducer arrays 30 to generate the TTField. The transducer arrays 30, leads 50, hub 42, cable 54, and electric field generator 58 may be constructed as described in "CONNECTOR FOR DETACHABLE ARRAY" in U.S. patent application Ser. No. 17/490,120 filed on Sep. 30, 2021, the entire content of which is hereby incorporated herein in its entirety.

Figure 2A:
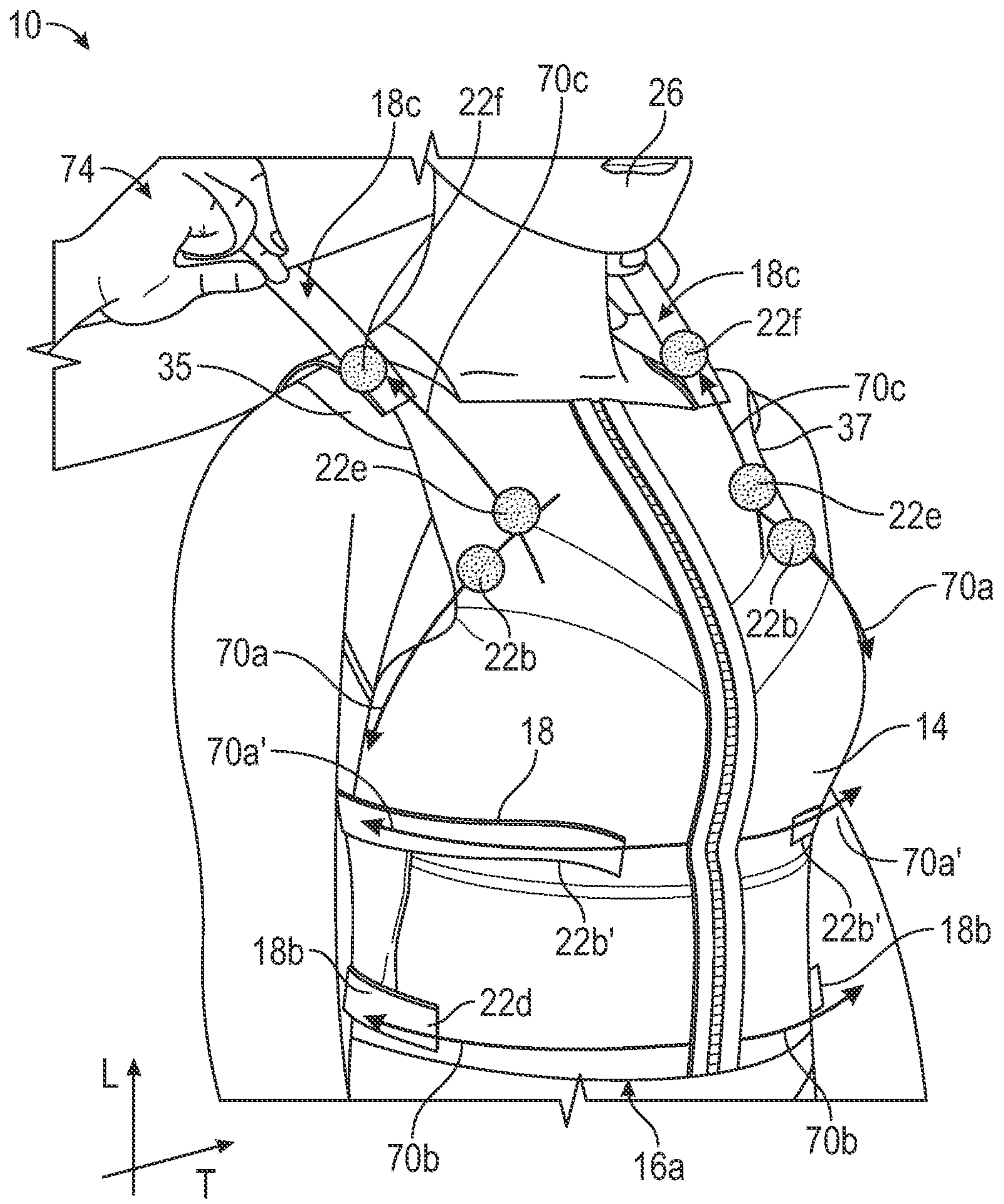
FIG. 2A is a front perspective view of an exemplary embodiment of a garment having a first adjustment assembly constructed in accordance with the present disclosure.

Referring now to FIG. 2A, shown therein is a diagram of an exemplary embodiment of the garment 10 being worn by the patient 26 further comprising a third adjustment assembly 18*c*. In one embodiment, the third adjustment assembly 18*c* is a shoulder strap. In the example shown, the garment 10 includes two of the third adjustment assemblies 18*c* that are spaced apart so as to be positioned on either side of the patient's neck. In one embodiment, a first of the third adjustment assemblies 18*c* may be positioned on the right side 35 of the garment 10 while a second of the third adjustment assemblies 18*c* may be positioned on the left side 37 of the garment 10.

In one embodiment, the third adjustment assembly 18*c* is adjustably secured to the support layer 14 at a sixth connection point 22*e* and a seventh connection point 22*f* such that adjustment of the third adjustment assembly 18*c* varies a spacing between the sixth connection point 22*e* and the seventh connection point 22*f* thereby varying a tension of the support layer 14. In one embodiment, the third adjustment assembly 18*c* is adjustable between a first position exerting a fourth force 70*c* in a direction extending from the sixth connection point 22*e* to the seventh connection point 22*f*, and a second position. However, it will be understood that the fourth force 70*c* may be exerted in a direction extending from the seventh connection point 22*f* to the sixth connection point 22*e*.

The sixth connection point 22*e* and the seventh connection point 22*f* may be different connection points 22 than the first, second, third, fourth, and/or fifth connection point 22*a*, 22*b*, 22*b*', 22*c*, and/or 22*d*. In one embodiment, the seventh connection point 22*f* is vertically displaced in the longitudinal axis L above the first vertical position of the first connection point 22*a* and a fifth vertical position of the sixth connection point 22*e*. The sixth connection point 22*e* may be at a fifth horizontal position substantially aligned with the fourth connection point 22*c* at a sixth horizontal position along the transverse axis T. In one embodiment, the sixth connection point 22*e* and the seventh connection point 22*f* are vertically displaced above (towards the direction of the head) the first connection point 22*a* and the second connection point 22*b*. In one embodiment, the second connection point 22*b* and the sixth connection point 22*e* may be the same or may substantially overlap.

Further shown in FIG. 2A is an adjustment of the third adjustment assembly 18*c* to the first position exerting the fourth force 70*c* on the support layer 14. Adjusting the third adjustment assembly 18*c* may be performed by the patient 26 or by a third-party 74, such as by a medical professional or by another person, for example. Adjusting the third adjustment assembly 18*c* may be performed, as shown, by the third-party 74 for convenience or for fitting of the garment 10 to the patient 26 by a medical professional; however, the patient 26 may perform the step of adjusting the third adjustment assembly 18*c*.

Figure 2B:
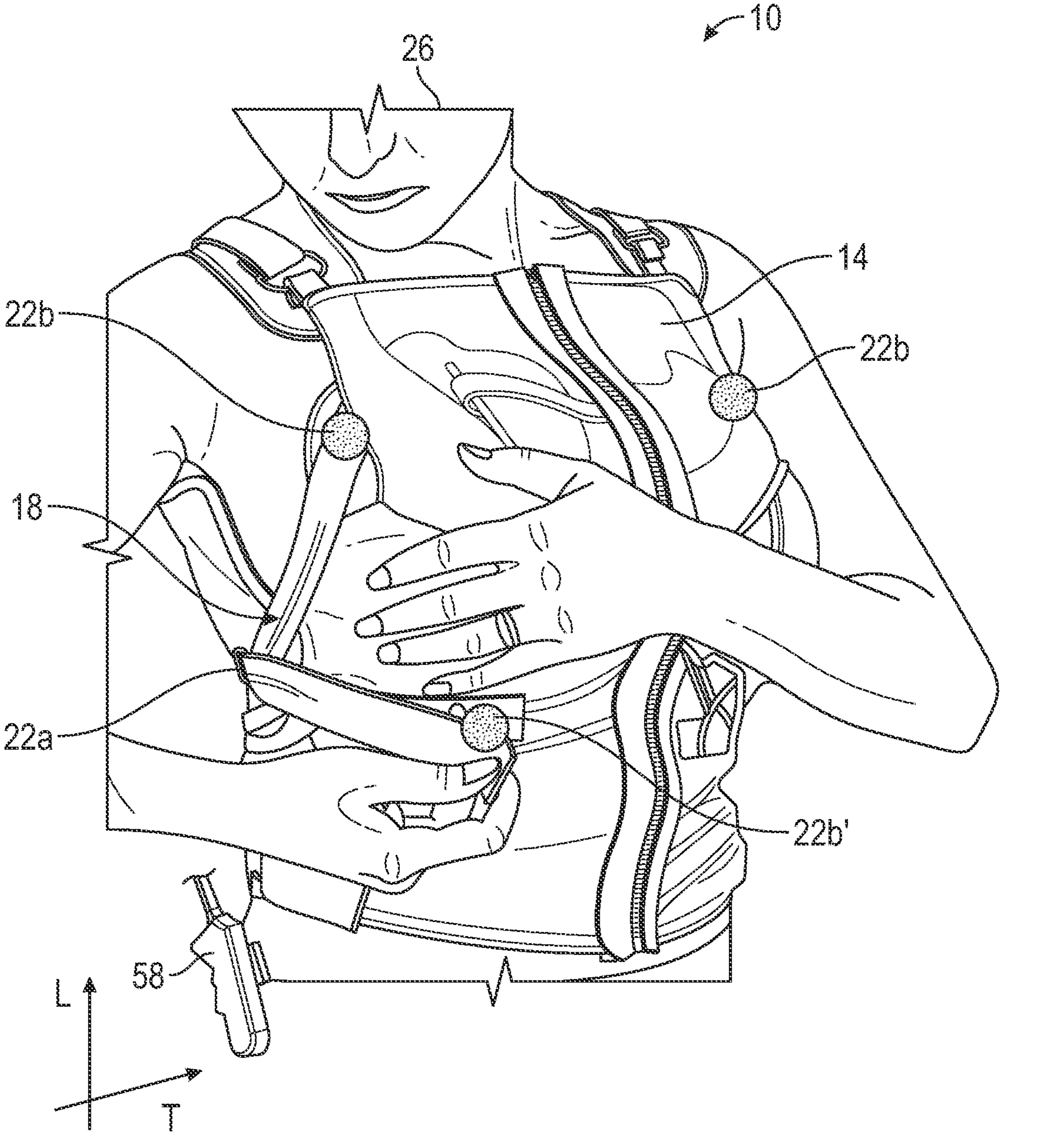
FIG. 2B is a front perspective view of an exemplary embodiment of a garment having a second adjustment assembly constructed in accordance with the present disclosure.

Referring now to FIG. 2B, shown therein is an illustration of an exemplary embodiment of the garment 10 as worn by the patient 26 wherein the first adjustment assembly 18 is adjusted to the first position exerting the first force 70*a* on the support layer 14. Adjusting the third adjustment assembly 18*c* may be performed by the patient 26 or by a third-party 74, such as by a medical professional or by another person, for example. In this example, the first adjustment assembly 18 is configured to apply the first force 70*a* on the support layer 14 so as to increase an amount of force applied to the patient 26 by the support layer 14 in a treatment region adjacent to the second connection point 22*b*. The second connection point 22*b* is preferably positioned adjacent to a concave part of the patient 26, such as a location above the patient's breast. When the first transducer array 30*a* is positioned on the patient's breast, as shown in FIG. 1A for example, tightening the first adjustment assembly 18 causes the support layer 14 to apply increased pressure onto the first transducer array 30*a* so as to form and maintain a connection between the first transducer array 30*a* and the patient's skin.

Figure 2C:
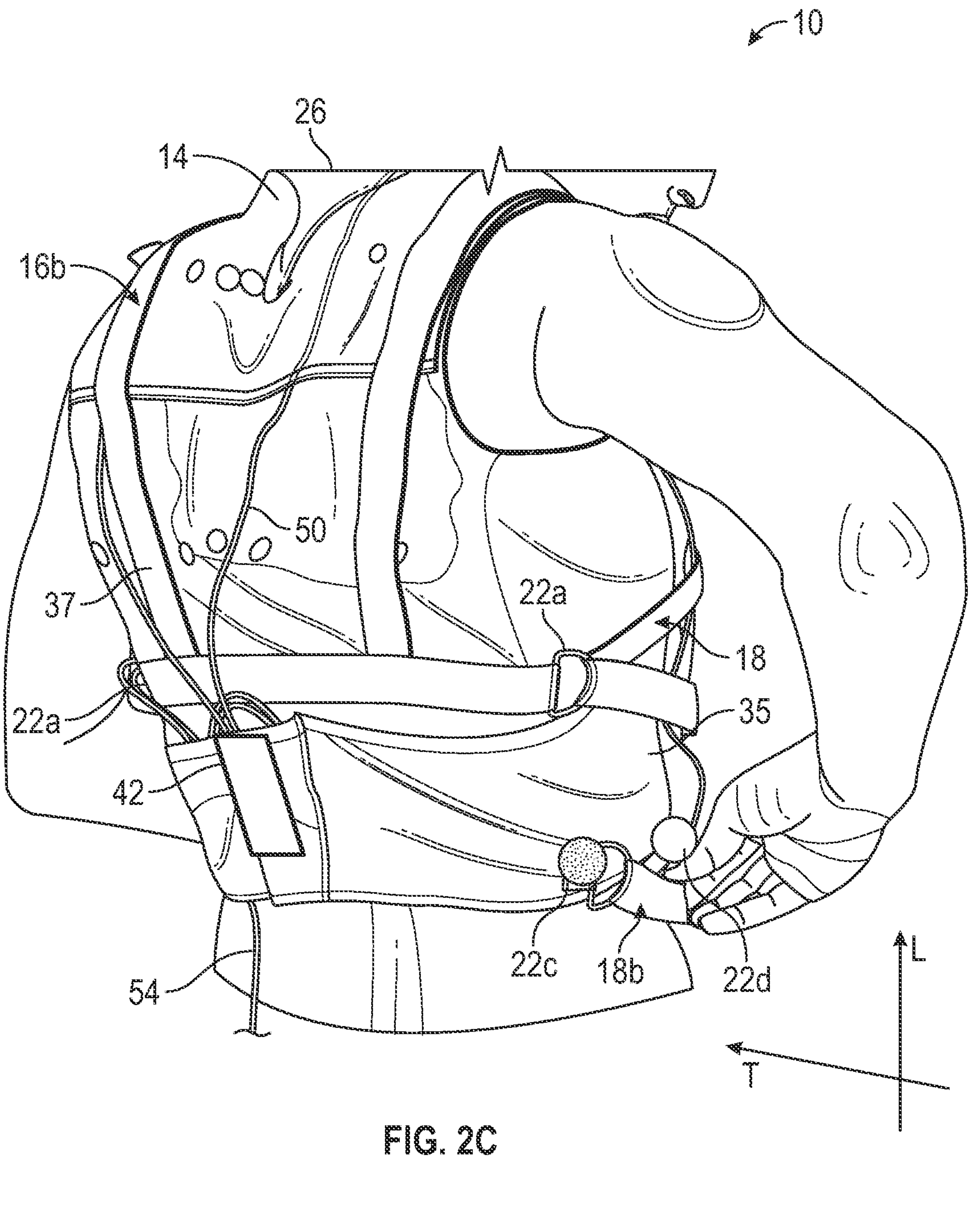
FIG. 2C is a rear perspective view of an exemplary embodiment of a garment having a third adjustment assembly constructed in accordance with the present disclosure.

Referring now to FIG. 2C, shown therein is an illustration of an exemplary embodiment of the garment 10 as worn by the patient 26 wherein the second adjustment assembly 18*b* is adjusted to the first position exerting the third force 70*b* on the support layer 14. Adjusting the second adjustment assembly 18*b* may be performed by the patient 26 or by a third-party 74, such as by a medical professional or by another person, for example.

Referring to FIGS. 1A-1B and FIGS. 2A-2C, generally, the first and second adjustment assemblies 18, 18*b* and connection points 22*a-n* are illustrated as being on the right side 35 of the garment 10, however, it should be understood that the adjustment assemblies 18 and connection points 22*a-n* are not limited to being on the right side 35 of the garment 10 and may be on the left side 37 of the garment instead of, or in addition to, being on the right side 35. In other words, while FIGS. 1A-2C are shown as having the first and second adjustment assemblies 18, 18*b* on the right side 35 of the garment 10, additional adjustment assemblies 18 may be placed at similar, mirrored locations on the left side 37 of the garment 10. In some embodiments, the garment 10 may have six adjustment assemblies 18, three on the right side 35 and three on the left side 37 of the garment 10.

Additionally, while only three adjustment assemblies 18 are shown on the right-hand side of the patient 26, additional adjustment assemblies 18 may be included on the garment 10 to vary additional connection points 22 on the support layer 14 resulting in additional forces 70 being applied to the support layer 14 to apply pressure to the transducer array(s) 30.

Figure 3B:
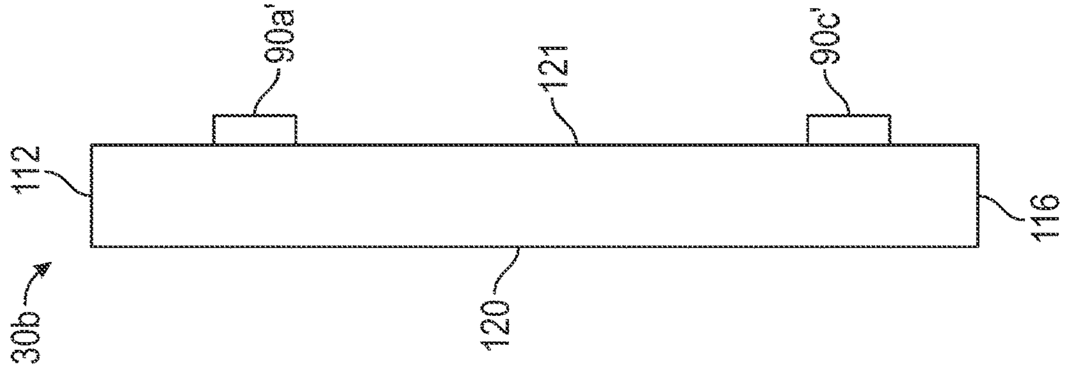
FIG. 3B is a side plan view of an exemplary embodiment of a transducer array constructed in accordance with the present disclosure.
Figure 3A:
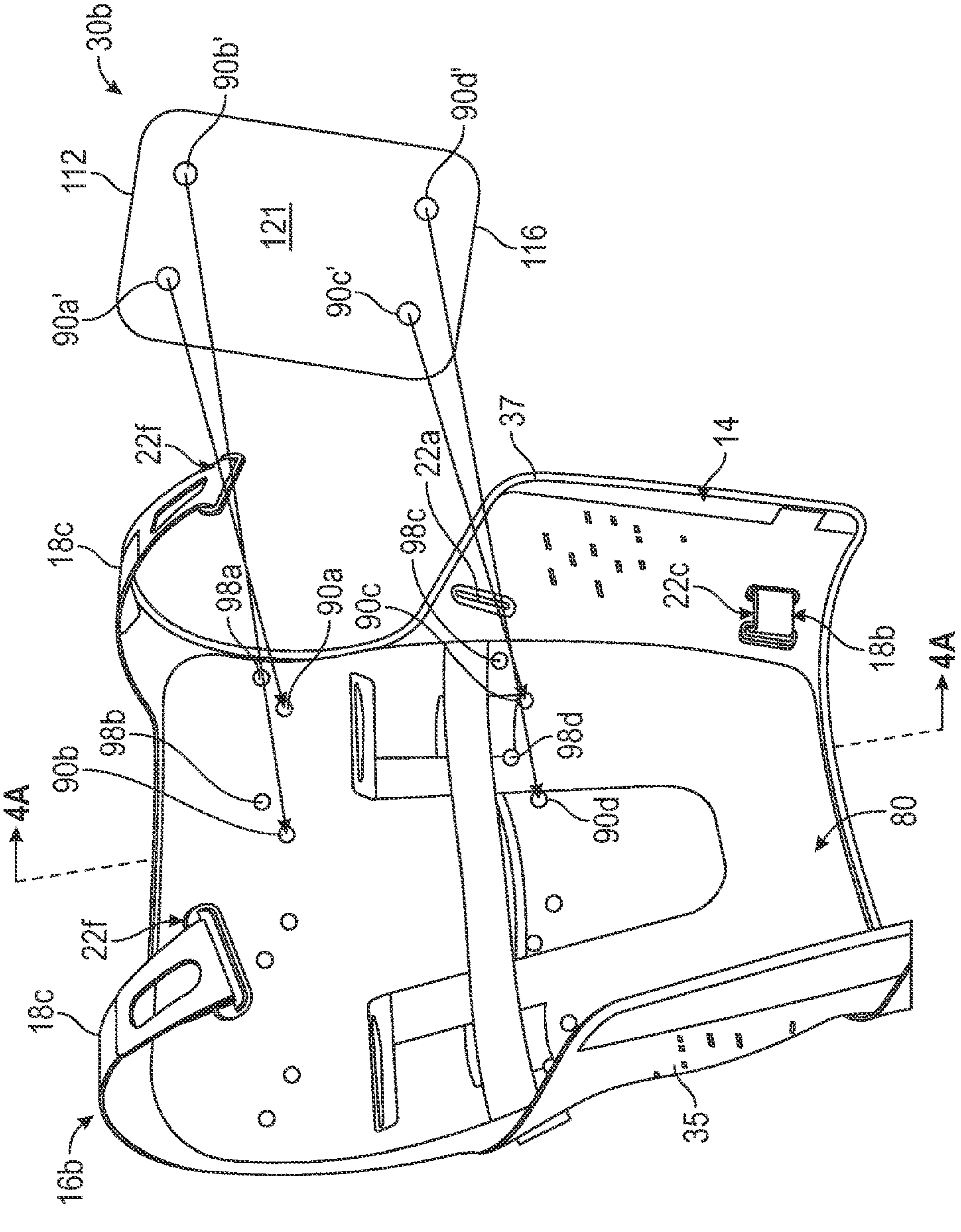
FIG. 3A is a perspective view of an exemplary embodiment of a back portion of a garment constructed in accordance with the present disclosure.

Referring now to FIG. 3A, shown therein is an illustration of an exemplary embodiment of the back portion 16*b* of the garment 10 constructed in accordance with the present disclosure. The back portion 16*b* may have a skin-facing surface 80. The garment 10 may further include one or more transducer array fastener 90*a-n*, collectively referred to as transducer array fasteners 90 and singly as transducer array fastener 90. For exemplary purposes, the garment 10 shown in FIG. 3A, includes first, second, third, and fourth transducer array fasteners 90*a-d* positioned on the skin-facing surface 80 of the back portion 16*b*.

In one embodiment, the transducer array fasteners 90 may be attached to the support layer 14 at predetermined locations. The predetermined location may generally be selected such that an extent of the area bound by the location of each transducer array fastener 90 substantially covers a treatment area of the patient 26. While the garment 10 is shown as including only four transducer array fasteners 90*a-d*, it is understood that the garment 10 could include a greater or lesser number of transducer array fasteners 90*a-n*.

Also shown in FIGS. 3A and 3B is a second transducer array 30*b*. The second transducer array 30*b* has a skin-facing surface 120 and a garment-facing surface 121. The second transducer array 30*b* has a top edge 112 and a bottom edge 116. The second transducer array 30*b* includes one or more complementary array fasteners 90', shown as first, second, third, and fourth complementary array fasteners 90*a'-d'*, positioned on the garment-facing surface 121 of the second transducer array 30*b* and operable to be coupled to corresponding ones of the transducer array fasteners 90 of the support layer 14. For example, as depicted in FIG. 3A, the first, second, third, and fourth complementary array fasteners 90*a'*, 90*b'*, 90*c'*, 90*d'* are operable to be coupled to the first, second, third, and fourth transducer array fasteners 90*a*, 90*b*, 90*c*, 90*d*, respectively.

Each fastener set, e.g., pair of transducer array fastener 90 and complementary array fastener 90', may be constructed of any fastener that can hold and support the second transducer array 30*b*. For example, each fastener set may comprise one or more of a hook and loop fastener, snap fastener, tape or double-sided tape, and/or the like.

In one embodiment, the garment 10 further includes one or more second transducer array fasteners 98*a-n*, depicted as exemplary first, second, third, and fourth second transducer array fasteners 98*a-d*. The second transducer array fasteners 98 are operable to be coupled to corresponding ones of the complementary array fasteners 90'. For example, the first, second, third, and fourth second transducer array fasteners 98*a*, 98*b*, 98*c*, 98*d* may be operable to be coupled to the first, second, third, and fourth complementary array fasteners 90*a'*, 90*b'*, 90*c'*, 90*d'*, respectively. The first, second, third, and fourth second transducer array fasteners 98*a-d* may be offset from the transducer array fasteners 90. For example, the offset may be in a range from about ¼ inch to about ½ inch. The offset may be along the longitudinal axis L, the transverse axis T, or along a combination of both the longitudinal axis L and the transverse axis T By attaching the second transducer array fasteners 98 at a different predetermined location on the support layer 14 as the transducer array fasteners 90, the patient 26 can easily move the second transducer array 30*b* from a first position, where the complementary array fasteners 94 are coupled to the transducer array fasteners 90, to a second position where the complementary array fasteners 94 are coupled to the second transducer array fasteners 98. The second transducer array 30*b* in the first position may be positioned over an overlapping yet different treatment area as the second transducer array 30*b* in the second position. In other embodiments, the treatment area of the second transducer array 30*b* in the first position may coincide with at least a portion of the treatment area of the second transducer array 30*b* in the second position.

In some embodiments, the treatment area of the second transducer array 30*b* in the first position and the treatment area of the second transducer array 30*b* in the second position are both selected to target the same target area within the patient 26; however, in other embodiments, the treatment area of the second transducer array 30*b* in the first position and the treatment area of the second transducer array 30*b* in the second position are selected to target different target areas within the patient 26

Figure 4B:
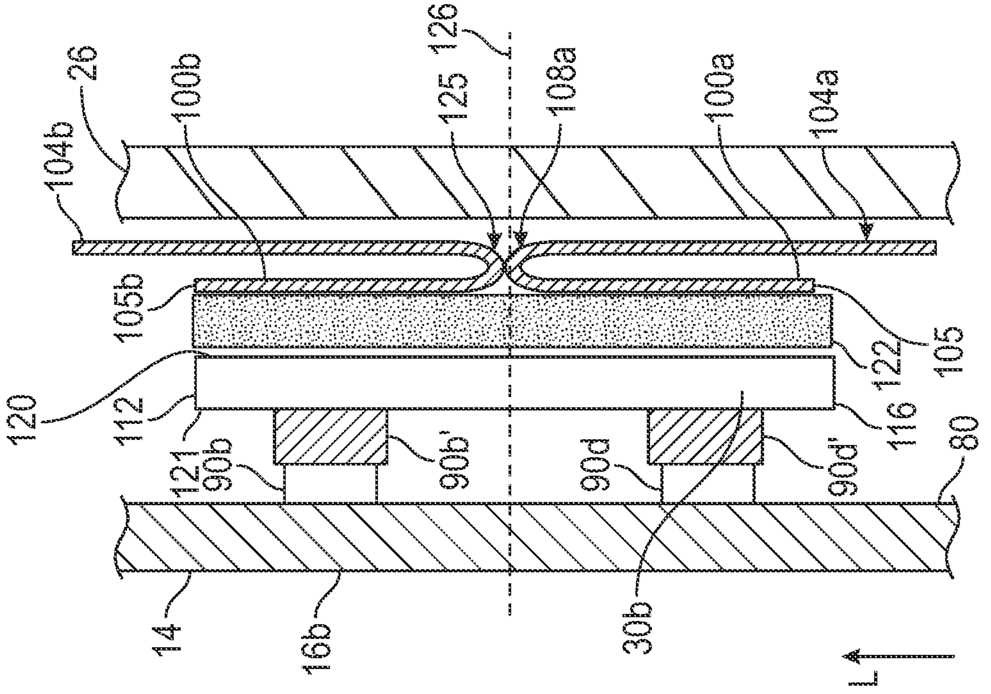
FIG. 4B is a partial cross-sectional view of another exemplary embodiment of the back portion of the garment receiving a transducer array on a patient constructed in accordance with the present disclosure.
Figure 4A:
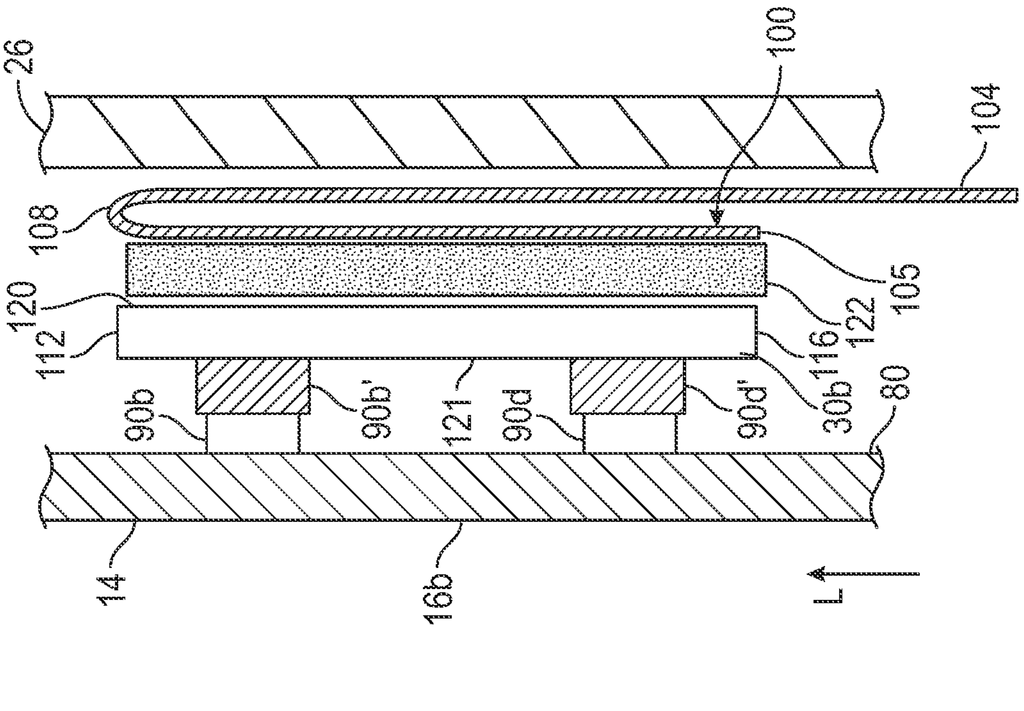
FIG. 4A is a partial cross-sectional view of an exemplary embodiment of a back portion of a garment receiving a transducer array on a patient constructed in accordance with the present disclosure.

Referring now to FIG. 4A, shown therein is a cross-sectional diagram of an exemplary embodiment of the second transducer array 30*b* having a protective layer 100 disposed against the second transducer array 30*b* along the longitudinal axis L. As shown in FIG. 4A, the garment 10 may be configured to be applied to the patient 26 thereby placing the protective layer 100 against the patient's skin. As shown in FIG. 4A, the support layer 14 is shown with the first and second transducer array fasteners 90*b*, 90*d* connected to corresponding ones of the first and second complementary array fasteners 90*b'*, 90*d'*, respectively. The first and second complementary array fasteners 90*b*', 90*d*' are shown as fixed to the second transducer array 30*b*. In one embodiment, the protective layer 100 is applied to the skin-facing surface 120 of the second transducer array 30*b*.

Figure 4C:
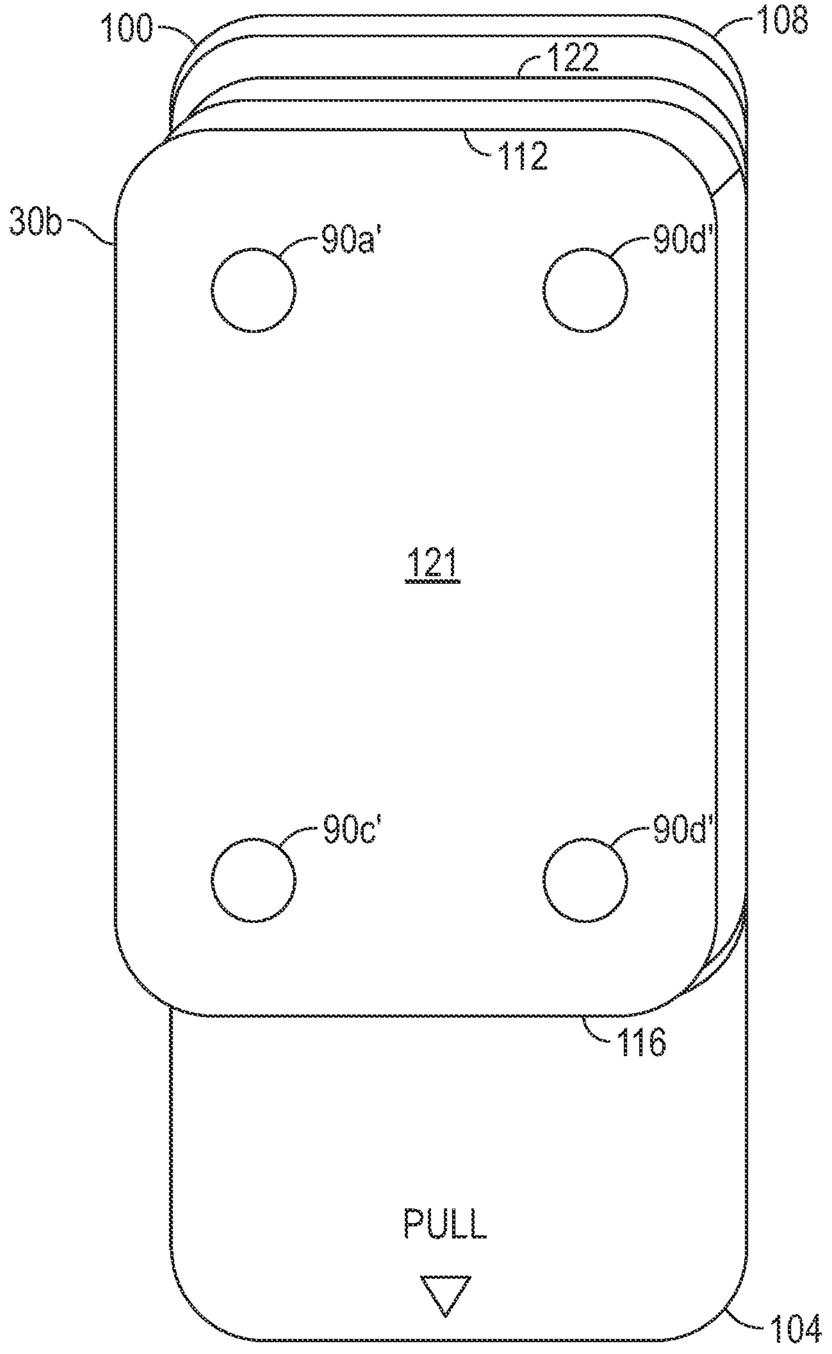
FIG. 4C is a perspective side view of an exemplary embodiment of components of a garment constructed in accordance with the present disclosure.

As shown in FIGS. 4A, 4B, and 4C, in some embodiments, the skin-facing surface 120 may be composed of or at least partially coated with a medical gel, such as medical gel layer 122. In these embodiments, the medical gel layer 122 may be disposed between the skin-facing surface 120 and the protective layer 100.

In one embodiment, the protective layer 100 may cover at least a portion of the second transducer array 30*b* that when the protective layer 100 is removed, such as by the patient 26, the second transducer array 30*b* is adhered to the patient's skin on or over the target area after the garment 10 is placed onto the patient 26.

In one embodiment, the protective layer 100 protects the second transducer array 30*b* and the medical gel layer 122 from potential damage, such as inadvertent adhesion to itself or other objects prior to the garment 10 being placed onto the patient. Further, protective layer 100 protects the medical gel layer 122 from loss of adhesion due to exposure moisture loss of the medical gel in the medical gel layer 122. The protective layer 100 may be removed by the patient 26 after the garment 10 is placed onto the patient 26, but before the second transducer array 30*b* receives an electrical signal from the electric field generator 58. In one embodiment, the protective layer 100 is an electric insulator covered by a non-stick coating, such that the protective layer 100 prevents or substantially reduces accidental application of a TTField to the patient 26 before the second transducer array 30*b* is attached to the patient 26.

In one embodiment, an adhesive may be used between the second transducer array 30*b* and the protective layer 100 such that application of the second transducer array 30*b*, having the protective layer 100 already applied thereto, to the support layer 14 may be performed without the protective layer 100 separating from the second transducer array 30*b*. In one embodiment, the second transducer array 30*b* does not include an attaching component (e.g., a cohesive or adhesive component), other than, in some embodiments, the medical gel, between the second transducer array 30*b* and the protective layer 100 and/or the patient 26.

In one embodiment, as shown in FIG. 4A, the protective layer 100 has a first end 105 in contact with and/or covering the medical gel layer 122, and a second end 108 that curves in a direction away from the first end 105. The protective layer 100 may have, or be connected to, a release member 104, which is connected to the second end 108 and which may be positioned parallel to the first end 105. In one embodiment, the release member 104 may extend past an outer edge of the support layer 14, such as along the longitudinal axis L. In one embodiment, the protective layer 100 and the release member 104 may be contiguous and formed of the same, flexible, material. In one embodiment, the protective layer 100, and/or the release member 104, are formed of a non-conductive material. In one embodiment, the release member 104 and the protective layer 100 may form a U-shape or a J-shape. In one embodiment, the release member 104 is positioned adjacent to the first end 105 of the protective layer 100. In one embodiment, at least a portion of the release member 104 is positioned adjacent to the first end 105 of the protective layer 100. While the second end 108 of the protective layer 100 is shown positioned proximate to the top edge 112 of the second transducer array 30*b* in FIG. 4A, it should be understood that the second end 108 may be positioned and/or have an orientation offset from or otherwise different from the position or orientation of the top edge 112.

In one embodiment, in use, when the patient 26, or a third-party, pulls the release member 104, such as in an opposing direction of the second end 108 of the protective layer 100, the release member 104 disengages the protective layer 100 from the second transducer array 30*b* and/or the medical gel layer 122, thereby causing the second transducer array 30*b* and/or the medical gel layer 122 to come into contact with the patient's skin. As shown in FIG. 4A, as a force is exerted on the release member 104 in a downward direction along the longitudinal axis L, the protective layer 100 at the second end 108 adjacent the top edge 112 of the second transducer array 30*b* is caused to peel away from the second transducer array 30*b* and/or the medical gel layer 122, followed by the first end 105 of the protective layer 100 being caused to peel away from the second transducer array 30*b* and/or the medical gel layer 122.

Referring now to FIG. 4B, shown therein is a cross-sectional diagram of an exemplary embodiment of the second transducer array 30*b* having a first protective layer 100*a* and a second protective layer 100*b* disposed against the second transducer array 30*b* and/or the medical gel layer 122 and being co-planar along the longitudinal axis L. The first protective layer 100*a* and the second protective layer 100*b* may be constructed similar to the protective layer 100 of FIG. 4A except as described below. The first protective layer 100*a* and the second protective layer 100*b* may be applied to the skin-facing surface 120, or to the medical gel layer 122, of the second transducer array 30*b*. Here, a second end 108*a* of the first protective layer 100*a* does not extend to the top edge 112 of the second transducer array 30*b*, but extends to a midline 126 different from the top edge 112 and the bottom edge 116. Further, the second protective layer 100*b* is inversed relative to the first protective layer 100*a*. For example, the first protective layer 100*a* may extend upwards from the bottom edge 116 to the midline 126 of the second transducer array 30*b* such that the second end 108*a* of the first protective layer 100*a* is at the midline 126, and the second protective layer 100*b* extends downward from the top edge 112 to the midline 126 of the second transducer array 30*b* such that a bottom 125 of the second protective layer 100*b* is at the midline 126. A first release member 104*a* may be attached to the second end 108*a* of the first protective layer 100*a* and extend downward as described with regards to the release member 104. In one embodiment, the first release member 104*a* and the first protective layer 100*a* may form a U-shape or a J-shape. In one embodiment, at least a portion of the first release member 104*a* is positioned adjacent to the first end 105 of the first protective layer 100*a*. A second release member 104*b* may attach to the bottom 125 of the second protective layer 100*b* and extend upward along the longitudinal axis L such that the second release member 104*b* may extend past the top edge 112 of the second transducer array 30*b* and past an edge of the support layer 14. In one embodiment the second release member 104*b* and the second protective layer 100*b* may form a U-shape or a J-shape. In one embodiment, at least a portion of the second release member 104*b* is positioned adjacent to the first end 105*b* of the second protective layer In one embodiment, in use, removing the protective layer 100 (FIG. 4A), the first protective layer 100*a*, and/or the second protective layer 100*b* (FIG. 4B), may be performed after the garment 10 has been placed on the patient 26 and/or after the adjustment assembly 18 has been adjusted such that the transducer arrays 30*a-n* are over the treatment areas and/or target regions of the patient. In one embodiment, the support layer 14 may include the aperture 48 (FIG. 1B) through which the release member 104 extends and removing the protective layer 100 may include pulling the release member 104, and thus the protective layer 100 through the aperture 48.

Figure 5:
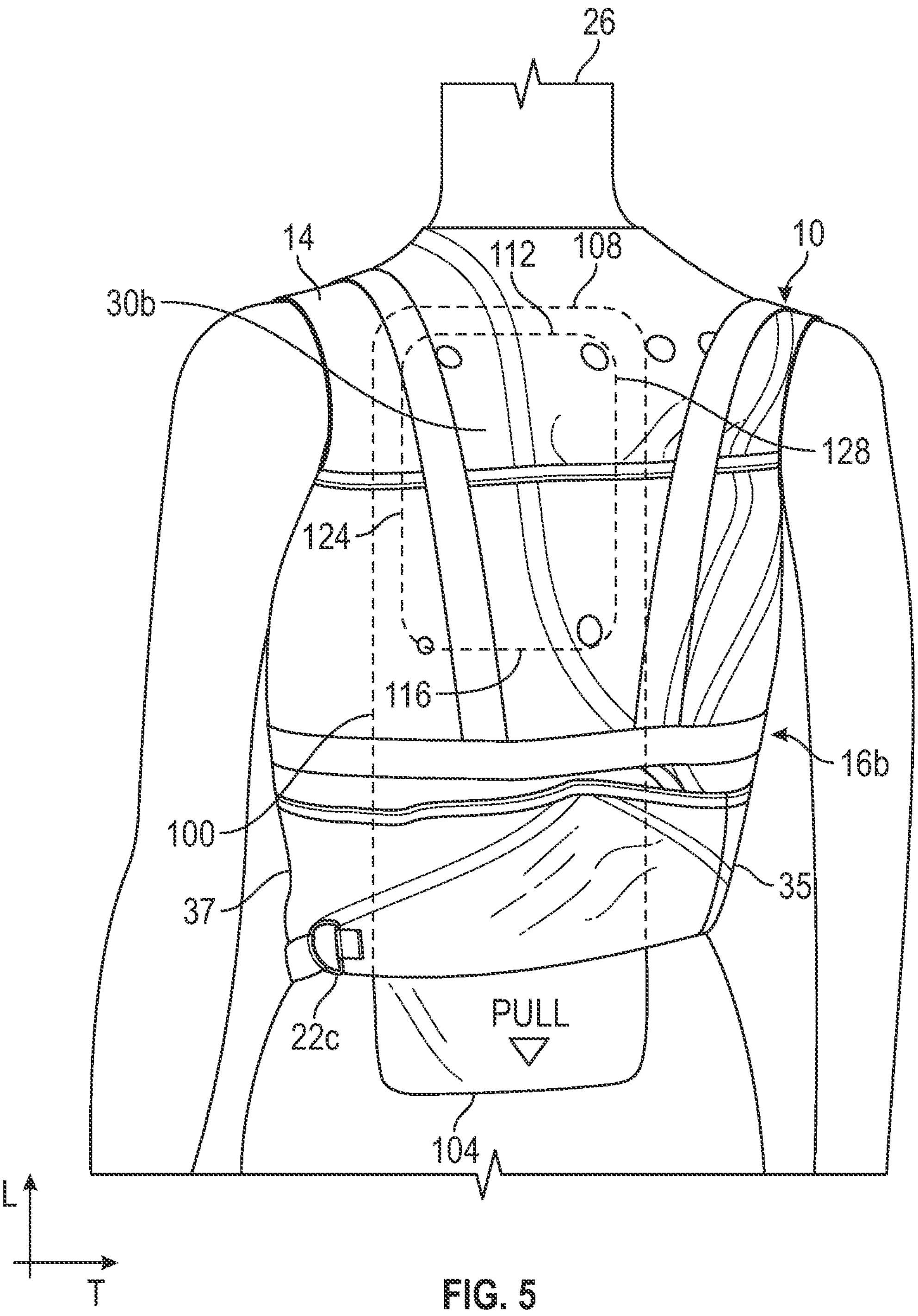
FIG. 5 is a rear perspective view of an exemplary embodiment of the back portion of the garment engaged with a transducer array constructed in accordance with the present disclosure.

Referring now to FIG. 5, shown therein is a perspective view of an exemplary embodiment of the patient 26 wearing the garment 10 having the second transducer array 30*b* attached to the back portion 16*b* of the support layer 14 and the protective layer 100 attached to the second transducer array 30*b*. The protective layer 100 has the release member 104 shown to extend beyond (such as below) the edge of the support layer 14 of the garment 10.

While the protective layer 100 and the release member 104 are shown as extending past side 124, side 128, and top edge 112 of the second transducer array 30*b*, in other embodiments, the protective layer 100 is coexistent with the side 124, the side 128, and the top edge 112 of the second transducer array 30*b*. In some embodiments where the second transducer array 30*b* includes the medical gel on the skin-facing surface 120, the protective layer 100 extends to cover at least the medical gel but does not necessarily extend as far as the side 124, the side 128, or the top edge 112 of the second transducer array 30*b*.

While the release member 104 has generally been described as extending past the support layer 14 or past the garment 10, it is understood that in some embodiments, the release member 104 may extend beyond the second transducer array 30*b* but may not extend beyond the support layer 14 or the garment 10, and in some embodiments the release member 104 may be the same size as or smaller than the second transducer array 30*b*.

As shown in FIGS. 4A-5, the release member 104 extends in an orientation of a substantially vertical direction along the longitudinal axis L; however, in other embodiments, the release member 104 may extend in the orientation of a substantially horizontal direction along the transverse axis T. In this embodiment, the release member 104 is attached to a side other than the second end 108 of the protective layer 100 and extends in the horizontal direction. In other embodiments, the protective layer 100 and the release member 104 may have other orientations than vertical and horizontal.

The following is a number list of non-limiting illustrative embodiments of the inventive concepts disclosed herein:

Illustrative Embodiment 1. A garment, comprising: a support layer configured to be worn by a patient, the support layer sized and dimensioned to cover at least a portion of the patient; a first connection point associated with the support layer, the first connection point disposed at a first vertical position and a first horizontal position of the support layer; a second connection point associated with the support layer, the second connection point disposed at a second vertical position and a second horizontal position of the support layer, the second vertical position being vertically displaced from the first vertical position, the second horizontal position being horizontally displaced from the first horizontal position; and an adjustment assembly adjustably secured to the support layer at the first connection point and the second connection point such that adjustment of the adjustment assembly varies the spacing between the first connection point and the second connection point to vary tension of the support layer in at least a portion of a treatment area; the adjustment assembly adjustable between a first position and a second position; wherein the adjustment assembly in the first position exerts a force in a direction extending from the second connection point to the first connection point.

Illustrative Embodiment 2. The garment of Illustrative Embodiment 1, wherein the adjustment assembly is a first adjustment assembly, and further comprising: a third connection point associated with the support layer, the third connection point disposed at a third vertical position, and a third horizontal position, the third vertical position being vertically displaced below the first vertical position; a fourth connection point associated with the support layer, the fourth connection point disposed at a fourth vertical position and a fourth horizontal position, the fourth horizontal position being horizontally displaced from the third horizontal position; and a second adjustment assembly adjustably secured to the support layer at the third connection point and the fourth connection point such that adjustment of the second adjustment assembly varies the spacing between the third connection point and the fourth connection point to vary tension of the support layer; the second adjustment assembly adjustable between a third position and a fourth position, wherein the second adjustment assembly in the fourth position exerts a force in a direction extending from the fourth connection point to the third connection point.

Illustrative Embodiment 3. The garment of Illustrative Embodiment 2, wherein the third vertical position and the fourth vertical position are substantially aligned.

Illustrative Embodiment 4. The garment of Illustrative Embodiment 3, wherein the second adjustment assembly includes a waist strap.

Illustrative Embodiment 5. The garment of Illustrative Embodiment 1, wherein the adjustment assembly is a first adjustment assembly, and further comprising: a third connection point associated with the support layer, the third connection point disposed at a third vertical position and a third horizontal position; a fourth connection point associated with the support layer, the fourth connection point disposed at a fourth vertical position and a fourth horizontal position, the fourth vertical position vertically displaced above the third vertical position; and a second adjustment assembly adjustably secured to the support layer at the third connection point and the fourth connection point such that adjustment of the second adjustment assembly varies the spacing between the third connection point and the fourth connection point to vary tension of the support layer; the second adjustment assembly adjustable between a third position and a fourth position, wherein the second adjustment assembly in the fourth position exerts a force in a direction extending from the third connection point to the fourth connection point.

Illustrative Embodiment 6. The garment of Illustrative Embodiment 5, wherein the second adjustment assembly includes a shoulder strap.

Illustrative Embodiment 7. The garment of Illustrative Embodiment 5, wherein the portion of the treatment area is a first portion of the treatment area, and wherein adjustment of the second adjustment assembly varies the tension of the support layer in at least a second portion of the treatment area.

Illustrative Embodiment 8. The garment of Illustrative Embodiment 7, wherein the first portion of the treatment area and the second portion of the treatment area substantially coincide.

Illustrative Embodiment 9. The garment of Illustrative Embodiment 7, wherein the first portion of the treatment area and the second portion of the treatment area partially coincide.

Illustrative Embodiment 10. The garment of Illustrative Embodiment 1, wherein the support layer further includes one or more first transducer array fastener configured to receive a second transducer array fastener of a transducer array positioned within at least a portion of the treatment area.

Illustrative Embodiment 11. The garment of Illustrative Embodiment 10, further comprising the transducer array having the second transducer array fastener, the transducer array affixed to the support layer via the first transducer array fastener engaging the second bad fastener, the transducer array further operable to receive a TTField signal and generate a TTField based on the TTField signal.

Illustrative Embodiment 12. The garment of Illustrative Embodiment 1, wherein the adjustment assembly comprises a strap having a first end and a second end, the strap adjustably engaging the first connection point and the second connection point, the first end engaging the support layer at the first connection point, wherein the first end comprises a first fastener fastening the first end to the first connection point, and the second end comprises a second fastener.

Illustrative Embodiment 13. The garment of Illustrative Embodiment 1, wherein the adjustment assembly comprises a first fastener having a first snap member and a first receiving member configured to receive the snap member, one of the snap member and the receiving member affixed to the first connection point.

Illustrative Embodiment 14. A system, comprising: an electric field generator operable to generate a TTField signal; a hub electrically connected to the electric field generator; a first transducer array electrically connected to the hub and operable to generate a TTField based on the TTField signal; a second transducer array electrically connected to the hub and operable to generate a TTField based on the TTField signal, the second transducer array having a first transducer array fastener; and a garment, comprising: a support layer configured to be worn by a patient and disposed over the two or more transducer arrays, the support layer sized and dimensioned to cover at least a portion of a chest of the patient; and the support layer having one or more second transducer array fastener configured to receive the first transducer array fastener of the second transducer array; a first connection point associated with the support layer, the first connection point disposed at a first vertical position and a first horizontal position of the support layer; a second connection point associated with the support layer, the second connection point disposed at a second vertical position and a second horizontal position of the support layer, the second vertical position being vertically displaced from the first vertical position, the second horizontal position being horizontally displaced from the first horizontal position; and an adjustment assembly adjustably secured to the support layer at the first connection point and the second connection point such that adjustment of the adjustment assembly varies the spacing between the first connection point and the second connection point to vary tension of the support layer over at least one of the two or more transducer arrays associated with a treatment area; the adjustment assembly adjustable between a first position and a second position; wherein the adjustment assembly in the first position exerts a force in a direction extending from the second connection point to the first connection point.

Illustrative Embodiment 15. A method, comprising: applying a support layer of a garment to a patient so as to cover two or more transducer arrays associated with a treatment area, the support layer configured to be worn by the patient, the support layer sized and dimensioned to cover at least a portion of the patient, the support layer having a longitudinal axis and a transverse axis normal to the longitudinal axis; adjusting a position of a first connection point on the support layer relative to a second connection point on the support layer so as to apply a force to the support layer in a direction that is not aligned with either of the longitudinal axis or the transverse axis to vary tension of the support layer over a first transducer array of the two or more transducer arrays associated with at least a portion of a treatment area; and supplying an alternating current electric signal having a frequency between 50 kHz and 1 MHz to the two or more transducer arrays.

Illustrative Embodiment 16. The method of Illustrative Embodiment 15, wherein adjusting the position of the first connection point on the support layer relative to the second connection point on the support layer further comprises adjusting an adjustment assembly adjustably secured to the first connection point and the second connection point, the adjustment assembly adjustable between a first position and a second position; wherein the adjustment assembly in the first position is configured to apply the force to the support layer.

Illustrative Embodiment 17. The method of Illustrative Embodiment 15, further comprising: adjusting a position of a third connection point on the support layer relative to a fourth connection point on the support layer so as to apply a second force to the support layer in a direction that is substantially aligned with the transverse axis to vary tension of the support layer, wherein the third connection point is vertically displaced below the first connection point.

Illustrative Embodiment 18. The method of Illustrative Embodiment 17, wherein adjusting the position of the third connection point on the support layer relative to the fourth connection point on the support layer further comprising: adjusting a second adjustment assembly secured to the third connection point and the fourth connection point, the second adjustment assembly adjustable between a first position and a second position, wherein the second adjustment assembly in the third position is configured to apply the second force to the support layer.

Illustrative Embodiment 19. The method of Illustrative Embodiment 15, further comprising: adjusting a position of a third connection point on the support layer relative to a fourth connection point on the support layer so as to apply a second force to the support layer in a direction that is substantially aligned with the longitudinal axis to vary tension of the support layer over the first transducer array of the two or more transducer arrays associated with at least a second portion of the treatment area, wherein the third connection point is longitudinally displaced above the fourth connection point.

Illustrative Embodiment 20. The method of Illustrative Embodiment 19, wherein adjusting the position of the third connection point on the support layer relative to the fourth connection point on the support layer further comprising: adjusting a second adjustment assembly secured to the third connection point and the fourth connection point, the second adjustment assembly adjustable between a first position and a second position, wherein the second adjustment assembly in the third position is configured to apply the second force to the support layer.

Illustrative Embodiment 21. A garment, comprising: a support layer configured to be worn by a patient, the support layer sized and dimensioned to cover at least a portion of the patient and associated with a transducer array fastener; a transducer array having a skin-facing surface and a complementary array fastener associated with a surface opposite the skin-facing surface, the transducer array fastener operable to be coupled with the complementary array fastener, the transducer array having a first edge and a second edge opposite the first edge; and a protective layer disposed on the skin-facing surface of the transducer array, the protective layer having a release member extending from the protective layer adjacent to the first edge of the transducer array and extending beyond the second edge of the transducer array.

Illustrative Embodiment 22. The garment of Illustrative Embodiment 21, wherein the protective layer and the release member are formed from a contiguous material wherein the contiguous material forms a "U" shape.

Illustrative Embodiment 23. The garment of Illustrative Embodiment 21, wherein the protective layer and the release member are formed of a non-conductive material.

Illustrative Embodiment 24. The garment of Illustrative Embodiment 21, wherein the transducer array further comprises a medical gel disposed on the skin-facing surface of the transducer array and between the transducer array and the protective layer.

Illustrative Embodiment 25. The garment of Illustrative Embodiment 24, wherein the transducer array does not include an attaching component separate from the medical gel, the attaching component configured to attach the transducer array to the patient.

Illustrative Embodiment 26. The garment of Illustrative Embodiment 21, wherein the release member extends beyond the support layer.

Illustrative Embodiment 27. The garment of Illustrative Embodiment 21, wherein the first edge of the transducer array and the second edge of the transducer array are at least partially opposing.

Illustrative Embodiment 28. The garment of Illustrative Embodiment 21, wherein the transducer array is a first transducer array, the garment further comprising a second transducer array, and an electric field generator, the electric field generator operable to supply a TTField signal to each of the first transducer array and the second transducer array and cause the first transducer array and the second transducer array to generate a TTField based on the TTField signal.

Illustrative Embodiment 29. A garment, comprising: a support layer configured to be worn by a patient, the support layer sized and dimensioned to cover at least a portion of the patient and associated with a transducer array fastener; a transducer array having a first edge, a second edge, a skin-facing surface, and a complementary array fastener associated with a surface opposite the skin-facing surface, the transducer array fastener operable to be coupled with the complementary array fastener; a first protective layer disposed on the skin-facing surface of the transducer array, the first protective layer covering a first portion of the transducer array, and having a first release member extending from the first protective layer and extending beyond the second edge of the transducer array; and a second protective layer disposed on the skin-facing surface of the transducer array, the second protective layer covering a second portion of the transducer array, and having a second release member extending from the second protective layer and extending beyond the first edge of the transducer array.

Illustrative Embodiment 30. The garment of Illustrative Embodiment 29, wherein the first protective layer and the first release member are formed from a first contiguous material and the second protective layer and the second release member are formed from a second contiguous material.

Illustrative Embodiment 31. The garment of Illustrative Embodiment 29, wherein the first protective layer and the second protective layer are formed of a non-conductive material.

Illustrative Embodiment 32. The garment of Illustrative Embodiment 29, wherein the transducer array further comprises a medical gel disposed on the skin-facing surface of the transducer array and between the transducer array and the first protective layer and the second protective layer.

Illustrative Embodiment 33. The garment of Illustrative Embodiment 32, wherein the transducer array does not include an attaching component separate from the medical gel, the attaching component configured to attach the transducer array to the patient.

Illustrative Embodiment 34. The garment of Illustrative Embodiment 29, wherein the first release member and the second release member extend beyond the support layer.

Illustrative Embodiment 35. The garment of Illustrative Embodiment 29, wherein the first edge of the transducer array is a top of the transducer array and the second edge of the transducer array is a bottom of the transducer array.

Illustrative Embodiment 36. The garment of Illustrative Embodiment 29, wherein the transducer array has a midline between the first edge of the transducer array and the second edge of the transducer array, and wherein at least one of the first protective layer and the second protective layer extends beyond the midline.

Illustrative Embodiment 37. The garment of Illustrative Embodiment 29, wherein the transducer array is a first transducer array, the garment further comprising a second transducer array, and an electric field generator, the electric field generator operable to supply a TTField signal to each of the first transducer array and the second transducer array and cause the first transducer array and the second transducer array to generate a TTField based on the TTField signal.

Illustrative Embodiment 38. A method comprising: applying a support layer of a garment to a patient so as to apply a first transducer array to a treatment area such that the first transducer array and a second transducer array are associated with the treatment area, the support layer configured to be worn by the patient, the support layer sized and dimensioned to cover at least a portion of the patient, the support layer having the first transducer array attached thereto, the first transducer array having a skin-facing surface and a protective layer disposed on the skin-facing surface of the first transducer array, the protective layer having a release member between the protective layer and the patient and extending from the protective layer to at least the support layer; removing the protective layer by pulling the release member extending beyond the support layer until the protective layer is detached from the skin-facing surface of the first transducer array; and supplying an alternating current electric signal having a frequency between 50 kHz and 1 MHz to the first transducer array and the second transducer array.

Illustrative Embodiment 39. The method of Illustrative Embodiment 38, wherein the support layer further includes an adjustment assembly attached thereto, the adjustment assembly adjustable between a first position and a second position; the method further comprising, before removing the protective layer, adjusting the adjustment assembly such that the first transducer array and the second transducer array cover at least a portion of the treatment area.

Illustrative Embodiment 40. The method of Illustrative Embodiment 38, wherein the first transducer array further includes a medical gel disposed between the first transducer array and the protective layer, and wherein removing the protective layer further includes removing the protective layer by pulling the release member extending beyond an edge of the first transducer array until the medical gel is exposed and applicable to skin of the patient.

The foregoing description provides illustration and description, but is not intended to be exhaustive or to limit the inventive concepts to the precise form disclosed. Modifications and variations are possible in light of the above teachings or may be acquired from practice of the methodologies set forth in the present disclosure.

Even though particular combinations of features are recited in the claims and/or disclosed in the specification, these combinations are not intended to limit the disclosure. In fact, many of these features may be combined in ways not specifically recited in the claims and/or disclosed in the specification. Although each dependent claim listed below may directly depend on only one other claim, the disclosure includes each dependent claim in combination with every other claim in the claim set.

From the above description and examples, it is clear that the inventive concepts disclosed and claimed herein are well adapted to attain the advantages mentioned herein. While exemplary embodiments of the inventive concepts have been described for purposes of this disclosure, it will be understood that numerous changes may be made which will readily suggest themselves to those skilled in the art and which are accomplished within the spirit of the inventive concepts disclosed and claimed herein.

What is claimed is:

1. A garment, comprising:

a support layer configured to be worn by a patient, the support layer sized and dimensioned to cover at least a portion of the patient and associated with a transducer array fastener;

a transducer array having a skin-facing surface and a complementary array fastener associated with a surface opposite the skin-facing surface, the complementary array fastener operable to be coupled with the transducer array fastener, the transducer array having a first edge and a second edge opposite the first edge; and a protective layer disposed on the skin-facing surface of the transducer array, the protective layer having a release member extending from the protective layer adjacent to the first edge of the transducer array and extending beyond the second edge of the transducer array, wherein the protective layer and the release member are formed from a contiguous material wherein the contiguous material forms a "U" shape.

2. The garment of claim 1, wherein the protective layer and the release member are formed of a non-conductive material.

3. The garment of claim 1, wherein the transducer array further comprises a medical gel disposed on the skin-facing surface of the transducer array and between the transducer array and the protective layer.

4. The garment of claim 3, wherein the transducer array does not include an attaching component separate from the medical gel, the attaching component configured to attach the transducer array to the patient.

5. The garment of claim 1, wherein the release member extends beyond the support layer.

6. The garment of claim 1, wherein the first edge of the transducer array and the second edge of the transducer array are at least partially opposing.

7. The garment of claim 1, wherein the transducer array is a first transducer array, the garment further comprising a second transducer array, and an electric field generator, the electric field generator operable to supply a TTField signal to each of the first transducer array and the second transducer array and cause the first transducer array and the second transducer array to generate a TTField based on the TTField signal.

8. A garment, comprising:

a support layer configured to be worn by a patient, the support layer sized and dimensioned to cover at least a portion of the patient and associated with a transducer array fastener;

a transducer array having a first edge, a second edge, a skin-facing surface, and a complementary array fastener associated with a surface opposite the skin-facing surface, the transducer array fastener operable to be coupled with the complementary array fastener;

a first protective layer disposed on the skin-facing surface of the transducer array, the first protective layer covering a first portion of the transducer array, and having a first release member extending from the first protective layer and extending beyond the second edge of the transducer array, wherein the first protective layer and the first release member are formed from a contiguous material wherein the contiguous material forms a "U" shape; and a second protective layer disposed on the skin-facing surface of the transducer array, the second protective layer covering a second portion of the transducer array, and having a second release member extending from the second protective layer and extending beyond the first edge of the transducer array.

9. The garment of claim 8, wherein the second protective layer and the second release member are formed from a second contiguous material.

10. The garment of claim 8, wherein the first protective layer and the second protective layer are formed of a non-conductive material.

11. The garment of claim 8, wherein the transducer array further comprises a medical gel disposed on the skin-facing surface of the transducer array and between the transducer array and the first protective layer and the second protective layer.

12. The garment of claim 11, wherein the transducer array does not include an attaching component separate from the medical gel, the attaching component configured to attach the transducer array to the patient.

13. The garment of claim 8, wherein the first release member and the second release member extend beyond the support layer.

14. The garment of claim 8, wherein the first edge of the transducer array is a top of the transducer array and the second edge of the transducer array is a bottom of the transducer array.

15. The garment of claim 8, wherein the transducer array has a midline between the first edge of the transducer array and the second edge of the transducer array, and wherein at least one of the first protective layer and the second protective layer extends beyond the midline.

16. The garment of claim 8, wherein the transducer array is a first transducer array, the garment further comprising a second transducer array, and an electric field generator, the electric field generator operable to supply a TTField signal to each of the first transducer array and the second transducer array and cause the first transducer array and the second transducer array to generate a TTField based on the TTField signal.

17. A method comprising:

applying a support layer of a garment to a patient so as to apply a first transducer array to a treatment area such that the first transducer array and a second transducer array are associated with the treatment area, the support layer configured to be worn by the patient, the support layer sized and dimensioned to cover at least a portion of the patient, the support layer having the first transducer array attached thereto, the first transducer array having a skin-facing surface and a protective layer disposed on the skin-facing surface of the first transducer array, the protective layer having a release member between the protective layer and the patient and extending from the protective layer to at least the support layer, wherein the protective layer and the release member are formed from a contiguous material wherein the contiguous material forms a "U" shape;

removing the protective layer by pulling the release member extending beyond the support layer until the protective layer is detached from the skin-facing surface of the first transducer array; and supplying an alternating current electric signal having a frequency between 50 kHz and 1 MHz to the first transducer array and the second transducer array.

18. The method of claim 17, wherein the support layer further includes an adjustment assembly attached thereto, the adjustment assembly adjustable between a first position and a second position; the method further comprising, before removing the protective layer, adjusting the adjustment assembly such that the first transducer array and the second transducer array cover at least a portion of the treatment area.

19. The method of claim 17, wherein the first transducer array further includes a medical gel disposed between the first transducer array and the protective layer, and wherein removing the protective layer further includes removing the protective layer by pulling the release member extending beyond an edge of the first transducer array until the medical gel is exposed and applicable to skin of the patient.

* * * * *